(12) United States Patent
Briggs et al.

(10) Patent No.: US 7,399,895 B2
(45) Date of Patent: Jul. 15, 2008

(54) ALUMINUM PHOSPHATE-SUPPORTED GROUP 6 METAL AMIDE CATALYSTS FOR OLIGOMERIZATION OF ETHYLENE

(75) Inventors: John R. Briggs, Charleston, WV (US); David W. Butler, Destrehan, LA (US); Timothy T. Wenzel, Charleston, WV (US); William C. Brooks, St. Albans, WV (US); Teresa L. Fortin, Alum Creek, WV (US)

(73) Assignee: Union Carbide Chemicals & Plastics, Danbury, CT (US)

( * ) Notice: Subject to any disclaimer, the term of this patent is extended or adjusted under 35 U.S.C. 154(b) by 42 days.

(21) Appl. No.: 10/586,827

(22) PCT Filed: Feb. 24, 2005

(86) PCT No.: PCT/US2005/005841

§ 371 (c)(1), (2), (4) Date: Jul. 20, 2006

(87) PCT Pub. No.: WO2005/092503

PCT Pub. Date: Oct. 6, 2005

(65) Prior Publication Data

US 2007/0161503 A1    Jul. 12, 2007

Related U.S. Application Data

(60) Provisional application No. 60/553,675, filed on Mar. 16, 2004.

(51) Int. Cl.
*C07C 2/08* (2006.01)
*C07C 2/32* (2006.01)
*C08F 4/69* (2006.01)

(52) U.S. Cl. ........................ 585/513; 585/510; 526/161; 526/169; 526/348.2; 502/103; 502/120

(58) Field of Classification Search ................. 585/506, 585/513, 510; 526/161, 169, 348.2; 502/103, 502/120
See application file for complete search history.

(56) References Cited

U.S. PATENT DOCUMENTS 5,814,575 A * 9/1998 Reagen et al. .............. 502/117

\* cited by examiner

*Primary Examiner*—Caixia Lu

(57) ABSTRACT

A catalyst composition for the preparation of oligomeric and/or polymer derivatives of olefin monomers, said composition comprising a Group 6 metal amide complex, a Group 1, 2, 12, 13, or 14 metal hydrocarbyl composition or compound, and a solid support comprising aluminum phosphate.

6 Claims, 1 Drawing Sheet

ALUMINUM PHOSPHATE-SUPPORTED GROUP 6 METAL AMIDE CATALYSTS FOR OLIGOMERIZATION OF ETHYLENE

CROSS REFERENCE STATEMENT

This application claims the benefit of U.S. Provisional Application No. 60/553,675, filed Mar. 16, 2004.

BACKGROUND OF THE INVENTION

This invention relates generally to the preparation of trimers, tetramers, and polymers of ethylene catalyzed by derivatives of certain metal complexes.

The selective trimerization of ethylene to prepare primarily 1-hexene, and ultimately to form polymers therefrom, has been extensively studied and a number of catalysts developed. Examples include the well known chromium pyrrolide complexes, disclosed in U.S. Pat. Nos. 5,523,507, 5,786,431, and elsewhere; trialkylsilylamide-chromium (II) complexes on activated inorganic refractory compounds in combination with aluminum triallyl compounds, disclosed in U.S. Pat. No. 5,104,841; chromium diphosphines, disclosed in *Chem. Comm.* (2002) p 858; chromium cyclopentadieniyl catalysts as disclosed in *Angew. Chem. Int. Ed.* 38 (1999), p 428, *J. Poly. Sci.*, 10 (1972), p 2621, and *Applied Catalysis A; General* 255, (2003), p 355-359; silica supported trialkylsilylamide-chromium complexes in combination with isobutylalumoxane, disclosed in *J. Mol. Cat. A: Chemical*, 187, (2002), p 135-141; mixed heteroatomic compounds disclosed in *Chem, Comm.* (2003), p 334; tantalum compounds disclosed in *Angew. Chem. Int. Ed.*, 42, (2003), p 808-810; titanium cyclopentadiene catalysts such as those of *Angew. Chem, Int. Ed.*, 40, (2001), p 2516; and numerous others. In U.S. Pat. No. 5,137,994, a process for producing ethylene/1-hexene copolymers directly from ethylene using silica supported chromium compounds was disclosed. Control of polymer density was obtained by adjusting the ethylene/1-hexene ratio of the intermediate monomer mixture obtained in an initial trimerization.

Oligomerization and polymerization of higher olefins such as propylene and 1-butene is disclosed in U.S. Pat. No. 4,668,838. The general mechanism of trimerization is considered to involve metalloheptane ring formation and most likely agnostic assisted hydride transfer, as disclosed in *Angew. Chem. Int. Ed.*, 42, (2003), 808-810. The foregoing processes are highly useful for the selective formation of trimers in the substantial absence of higher oligomer or polymer formation. There remains a need for the discovery of processes for the selective formation of tetramers, especially 1-octene from ethylene.

Stepwise ethylene chain growth on aluminum alkyls was discovered in the 1950's by K. Ziegler et al. The reaction is normally conducted at temperatures in the range of 100°-200° C. under high ethylene pressure, typically 2000-4000 psi (14-28 MPa). At higher temperatures, a displacement reaction or cracking step competes with chain growth, producing α-olefins and regenerating aluminum alkyl compounds. For a review see, "Comprehensive Organometallic Chemistry: 1982, Pergammon Press, Vol. 7, Section 46. The process may be advanced by catalysts, both for the step-wise growth of the aluminum alkyl and the catalyzed displacement of α-olefins therefrom. Ziegler-Natta catalysts such as those discovered by Kaminsky et al. *Angew. Chem. Int. Ed. Engl.*, 1976, Vol. 15, pages 630-632 may be used to catalyze the growth process. This process is thought to involve active transition metal catalysts which promote the growth of the aluminum alkyl chains. Chain growth is terminated in the displacement or cracking step, principally by β-hydrogen- or β-alkyl-elimination to give a vinylic end group or by hydrogenolysis to give a paraffinic end group, thereby regenerating a catalytically active transition metal-hydride or alkyl and an aluminum-hydride or alkyl.

The manufacture of α-olefins using the foregoing step addition to aluminum alkyls is commercially practiced in large volume. Suitable processes operating at lower temperatures and pressures than those employed by early artisans are disclosed in U.S. Pat. No. 5,276,220 (using actinide metal metallocene based complexes, which unfortunately are radioactive, as catalysts) and in U.S. Pat. No. 5,210,338 (using metallocene based complexes of zirconium and hafnium).

A persistent problem of the foregoing step growth processes is the production of aluminum alkyls and the resulting α-olefin products having a narrow molecular weight distribution (Poisson distribution). In many such processes the products are undesirably broad, and best described by the Schulz-Flory statistical distribution. These statistical distributions are commonly known and defined by the equations: Poisson: $X_p = (x^p \cdot e^{-x})/p!$, and Schulz-Flory: $X_p = \beta(1+\beta)^{-p}$, where $X_p$ is the mole fraction with p added monomer units, x is the Poisson distribution coefficient equal to the average number of monomers added, and $\beta$ is the Schulz-Flory distribution coefficient. A typical Schultz-Flory distribution of α-olefins would provide a maximum of 15 percent 1-hexene and 17 percent 1-octene. Additionally, significant quantities of 1-decene and higher α-olefins ($C_{12-30}$ α-olefins) are produced, along with low molecular weight waxy polymers.

Despite the advance in the art encompassed by the foregoing known processes, a process that operates at milder temperatures and pressures to produce primarily trimers (1-hexene) and tetramers (1-octene), especially in a Poisson type distribution, while limiting less valuable butene, $C_{10-30}$ α-olefin, and low molecular weight polymer formation is still desired. The α-olefin products of the present process, especially 1-hexene and 1-octene are useful industrial chemicals employed to prepare alcohols and plastics, especially high molecular weight, linear low density, polyethylene.

Further desired is a process for preparing high molecular weight polymers and/or copolymers of ethylene and branch inducing α-olefins such as 1-hexene and/or 1-octene (linear low density polyethylene) directly from ethylene.

SUMMARY OF THE INVENTION

In accordance with this invention there is provided an improved catalyst composition for the preparation of oligomeric derivatives of olefin monomers, especially ethylene, comprising a Group 6 metal amide complex or compound, a Group 1, 2, 12, 13 or 14 metal hydrocarbyl composition or compound, and a solid support comprising aluminum phosphate.

Also provided is an improved process for the preparation of oligomeric derivatives of olefin monomers, especially ethylene, comprising contacting the olefin monomer or a mixture of olefin monomers under oligomer formation conditions with a catalyst composition comprising a Group 6 metal amide complex or compound, a Group 1, 2, 12, 13 or 14 metal hydrocarbyl composition or compound, and a solid support comprising aluminum phosphate.

In a further embodiment, there is provided a process for preparing high molecular weight polyethylene and/or short chain branched copolymers of ethylene and one or more $C_{6-8}$ α-olefins, preferably 1-octene, by the direct α-olefin formation and polymerization of ethylene with a catalyst composition comprising a Group 6 metal amide complex or compound, a Group 1, 2, 12, 13 or 14 metal hydrocarbyl composition or compound, and a solid support comprising aluminum phosphate.

In yet another embodiment of the invention there is provided a process for the catalytic oligomerization of ethylene to yield a mixture comprising a Poisson distribution of 1-hexene and 1-octene products, preferably a product mixture comprising greater than 10 percent 1-octene and less than 90 percent, preferably less than 80 percent, 1-hexene with less than 10 percent butene and $C_{10-30}$ α-olefin, and optionally polymer. Preferred catalysts are those comprising a Group 6 metal amide complex or compound, a Group 1, 2, 12, 13 or 14 metal hydrocarbyl composition or compound, and a solid support comprising aluminum phosphate.

In a final embodiment of the invention there is provided a polymerization process wherein the foregoing mixture of olefins prepared by the catalytic oligomerization of ethylene is polymerized to form a high molecular weight polymer with or without the addition of ethylene or other polymerizable comonomer, in the presence of the same catalyst used in the catalytic oligomerization and/or a different catalyst or catalyst mixture.

DETAILED DESCRIPTION OF THE INVENTION

Figure 1:
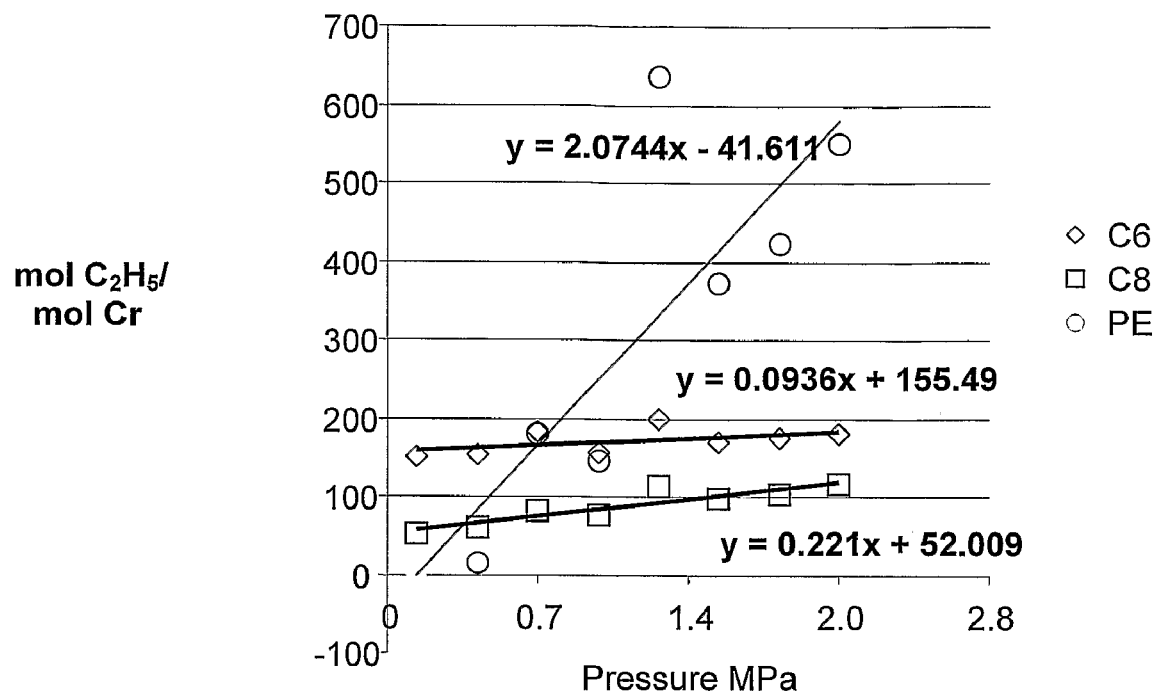
FIG. 1 gives conversions as a function of ethylene pressure for products prepared in Example 1.

All references to the Periodic Table of the Elements herein shall refer to the Periodic Table of the Elements, published and copyrighted by CRC Press, Inc., 2003. Also, any references to a Group or Groups shall be to the Groups or Groups reflected in this Periodic Table of the Elements using the IUPAC system for numbering groups. For purposes of United States patent practice, the contents of any patent, patent application, or publication referenced herein are hereby incorporated by reference in their entirety (or the equivalent US version thereof is so incorporated by reference) especially with respect to the disclosure of synthetic techniques, raw materials, and general knowledge in the art.

If appearing herein, the term "comprising" and derivatives thereof is not intended to exclude the presence of any additional component, step or procedure, whether or not the same is disclosed herein. In order to avoid any doubt, all compositions claimed herein through use of the term "comprising" may include any additional additive, adjuvant, or compound, unless stated to the contrary. In contrast, the term, "consisting essentially of" if appearing herein, excludes from the scope of any succeeding recitation any other component, step or procedure, excepting those that are not essential to operability. The term "consisting of", if used, excludes any component, step or procedure not specifically delineated or listed. The term "or", unless stated otherwise, refers to the listed members individually as well as in any combination. Unless stated to the contrary conventional in the art or implicit from the context, all parts and percents are based on weight.

Examples of α-olefins suitable for chain growth herein include, but are not limited, to $C_2$ to $C_6$ straight chain α-olefins or mixtures thereof, with ethylene being the preferred olefin.

Suitable Group 6 metal amide compounds for use as the catalyst component of the present invention include compounds corresponding to the following formula: $M(NR^1{}_2)_r X_{v-r}$ wherein M is a Group 6 metal, especially chromium in the +3 formal oxidation state;

$R^1$ independently in each occurrence is an alkyl group of from 3 to 20 carbons, a cycloalkyl group of from 5 to 20 carbons, an aryl or alkylaryl group of from 6 to 20 carbons, or a tri($C_{1-20}$)hydrocarbylsilyl group, and optionally two $R^1$ groups on the same or adjacent amide groups may be joined together thereby forming a heterocycloaliphatic ring, or an alkyl-, aryl-, cycloalkyl-, or trihydrocarbylsilyl-substituted derivative thereof;

X is an anionic ligand of up to 20 atoms not counting hydrogen, and optionally one or more X groups and/or one or more $NR^1{}_2$ groups may be joined together to form an aliphatic or aromatic ring, r is a number greater than 0 and less than or equal to v, and v is the valence of M.

Preferred $R^1$ groups include secondary or tertiary alkyl groups, aryl, alkylaryl, and trihydrocarbylsilyl groups of from 3 to 20 carbons, or two $R^1$ groups on a single amide together are a $C_{5-12}$ alkylene group. Most preferably $R^1$ each occurrence is isopropyl, cyclohexyl or trimethylsilyl.

Preferred X groups include hydride, halide, hydrocarbyl, trihydrocarbylsilyl, hydrocarbyloxy, and trihydrocarbylsiloxy of up to 10 atoms not counting hydrogen, most preferably chloride or methyl.

Examples of suitable Group 6 metal amide compounds include chromium tris(bis(trimethylsilyl)amide), chromium tris(diisopropylamide), chromium tris(diphenylamide), chromium tris(di(2-methylphenyl)amide), chromium tris(dicyclohexylamide), and chromium tris(2,2,6,6-tetramethylpiperdyl). Preferred Group 6 metal amide compounds are chromium tris(bis(trimethylsilyl)amide) and chromium tris (diisopropylamide). The group 6 metal amide compounds may be readily prepared by reaction of the corresponding trialkyl chromium compound with the lithium amide in an ether solvent followed by recovery from an aliphatic hydrocarbon, by the technique previously disclosed in *J.C.S., Dalton*, (1972), p 1580-1584, or by any other suitable technique. Highly desirably, the metal complex and the subsequent oligomerization or polymerization reaction is substantially devoid of Lewis base compounds such as ethers.

Mixtures of metal complexes of the foregoing type or mixtures thereof with other metal complexes may be employed if desired. In the manufacture of polymers, mixtures of metal complexes are preferably employed. In this manner, a catalyst that is most efficient for producing oligomers may be employed in combination, either in a separate reactor or the same reactor, with a catalyst (secondary catalyst) that is most efficient in producing copolymer products to optimize the formation of copolymeric products. Examples of suitable secondary metal complexes for use herein include the well known metallocene and constrained geometry titanium based metal complexes disclosed in U.S. Pat. Nos. 6,268,444, 5,965,756, 5,703,187, 5,866,704, 6,150,297, 6,555,634, 6,515,155, 6,613,921, and elsewhere.

Suitable Group 1, 2, 12, 13 or 14 metal hydrocarbyl compounds for use herein especially include lithium, magnesium, aluminum, zinc and tin compounds containing one or more hydrocarbyl ligand groups containing from 1 to 20 carbons in each hydrocarbyl group. Examples include trihydrocarbyl aluminums, dihydrocarbyl aluminum hydrides, dihydrocarbyl aluminum halides, dihydrocarbylaluminum hydrocarboxides, dihydrocarbyl zincs, tetrahydrocarbyl tins, alumoxanes, and mixtures thereof. Preferred metal hydrocarbyl compounds are those of Groups 12, 13 or 14. Specific non-limiting examples of suitable aluminum hydrocarbyl compounds (which are the most preferred metal hydrocarbyl compounds) include trialkylaluminum compounds such as trimethylaluminum triethylaluminum, tri-n-propylaluminum, tri-n-butylaluminium, tri-n-hexylaluminum, triisobutylaluminum, and alumoxanes such as methylalumoxane or triisobutylaluminum modified methalumoxane. Most highly preferred aluminum hydrocarbyl compounds are trimethylaluminums (TMA), triethylaluminum (TEA), and tri-isobutylaluminum (TIBA).

Suitable alumoxanes for use herein include polymeric or oligomeric alumoxanes, especially methylalumoxane, triisobutyl aluminum modified methylalumoxane, or isobutylalumoxane; neutral Lewis acid modified polymeric or oligomeric alumoxanes, such as the foregoing allylalumoxanes modified by addition of a $C_{1-30}$ hydrocarbyl substituted Group 13 compound, especially a tri(hydrocarbyl)aluminum- or tri(hydrocarbyl)boron compound, or a halogenated (including perhalogenated) derivative thereof, having from 1 to 10 carbons in each hydrocarbyl or halogenated hydrocarbyl group, more especially a perfluorinated tri(aryl)boron compound or a perfluorinated tri(aryl)aluminum compound.

Suitable supports comprise crystalline, semi-crystalline, and amorphous aluminum phosphate compounds, preferably highly amorphous aluminum phosphate. By the term "amorphous" is meant that the compound contains less than 60 percent preferably less than 50 percent crystallinity as determined by NMR or other suitable technique. Suitable aluminum phosphate materials may be prepared substantially according to the technique disclosed by Glemza, et al., ACS Symposium on Catalyst Supports: Chemistry, Formation and Characterization, Div. of Petroleum Chemistry, New York, Aug. 25-30, 1991, *Catalysis Today*, 14 (1992) 175-188, EP-A-215,336 as well as U.S. Pat. No. 6,461,415 or 6,036,762, by contacting a solution of an aluminum salt, especially aluminum nitrate, with a phosphorous containing compound such as phosphorus pentoxide, $Na_2H_2PO_5$, or phosphoric acid, forming a gel and removing the solvent. The aluminum phosphate may also be deposited as a surface coating on a solid substrate, especially a porous substrate such as silica or alumina, if desired. Generally, treatment (extraction) of the aluminum phosphate with ammonia or other extracting agent, leads to higher amounts of polymer formation.

Desirably, the amount of surface hydroxyl functionality of the resulting aluminum phosphate material is reduced to as low as possible by thoroughly drying or calcining the product prior to use. Suitable drying or calcining conditions include heating the material to a temperature from 100 to 600° C. for time periods from several minutes to several hours. Longer drying times are employed at lower drying temperatures.

Suitable aluminum phosphate compounds are those of the formula: $(P_2O_5)(Al_2O_3)_u$, wherein u is a number from 0.1 to 10. Nominal quantities of surface hydroxyl groups may be present on the aluminum phosphate, without substantial adverse consequence. Preferably the quantity of surface hydroxyl functionality is less than 10 ppm, most preferably less than 1.0 ppm.

Preferred aluminum phosphate compounds are those of the formula: $Al_xP_yO_4$ where x+y=2 and x is >0.2. Highly preferred compounds are those having a P/Al molar ratio from 0.6 to 1.0, preferably from greater than 0.90 to 1.0, and most preferably from 0.92 to 1.0. Compounds having higher P/Al molar ratio, especially ratios of approximately 1, are generally less crystalline or contain occluded crystalline regions thereby increasing the surface area and making them less subject to polymorphic transformations.

Most preferred aluminum phosphate compounds are substantially amorphous, three dimensional complexes corresponding to the formula:

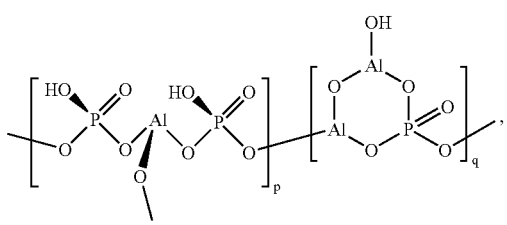

wherein p and q are each independently numbers from 1-100, preferably from 1 to 5. Greater degrees of calcination can result in more complete removal of hydroxyl functionality and formation of additional oxygen bridges between neighboring phosphorous and/or aluminum atoms.

Desirably, the aluminum phosphate has a particle size from 10 to 1000 μm, preferably from 50 to 500 μm. Highly desirably, the aluminum phosphate is essentially or mostly amorphous (no detectable crystallinity) and has a surface area from 100 to 500 m²/g, more preferably from 200 to 350 m²/g, a pore volume from 0.75 to 2.0 cm³/g, more preferably from 1.0 to 1.5 cm³/g, and a relatively large average pore size, preferably greater than 8.5 nm, more preferably greater than 10.0 nm, and most preferably greater than 15.0 nm.

The foregoing Group 6 metal complexes are activated to form the actual catalyst composition by combination with the hydrocarbylaluminum compound, and the support. The oligomerization process is conducted in the presence of the monomer to be oligomerized and optionally a diluent. Suitable diluents include liquid hydrocarbons such as $C_{6-10}$ alkanes or cycloalkanes, and mixtures thereof. Additional additives, such as a chain transfer agent, for example, hydrogen, used to control polymer chain length if polymerization is desired, may be present in the reaction as well, but are generally unnecessary. The resulting olefin products essentially follow the Poisson statistical distribution, generally comprising primarily trimer and tetramer products, and the process is characterized by low temperatures and pressures.

Desirably the process results in production of an olefin mixture comprising 1-hexene and 1-octene in which the weight ratio of 1-octene/1-hexene+1-octene is greater than 20 percent, preferably greater than 25 percent. Additionally preferably, the weight ratio of 1-hexene+1-octene to total alpha olefin reaction products is greater than 90 percent, more preferably greater than 95 percent. Highly desirably the quantity of polymer formed in the process is less than 60 percent of all products formed, preferably less than 50 percent.

Reaction temperatures for the oligomerization and polymerization process may vary from 20° to 150° C., preferably from 30° C. to 120° C. Use of higher temperatures tends to increase polymer formation. Preferred temperatures for forming mixtures consisting primarily of ethylene oligomers, especially 1-hexene and 1-octene are from 20 to 80° C., more preferably from 45 to 75° C.

Pressures in all of the foregoing processes may be varied from 10 to 1000 psig (70 kPa to 7 MPa), preferably from 20 to 500 psi (150 kPa to 3.4 MPa). Suitably, the quantity of ethylene is employed to control reactor pressure. Generally, the mole ratio of catalyst composition (based on amount of Group 6 metal) to metal hydrocarbyl compound may be varied from 0.01:1 to 10:1, preferably from 0.05:1 to 1:1, and more preferably is in the range from 0.1:1 to 0.5:1. Where alumoxane is used as the metal hydrocarbyl, the mole ratio of Group 6 metal compound to alumoxane, expressed as moles of total aluminum in the alumoxane, may range from 1/5 at high catalyst concentrations to 1/50,000 at low catalyst concentrations. The amount of aluminum phosphate employed is desirably equivalent to or in excess of the amount of Group 6 metal compound used. Generally molar ratios of aluminum phosphate to Group 6 metal compound from 1:1 to $1 \times 10^6$:1 are employed.

The various components of the catalyst composition may be added entirely at the initiation of the process, in portions throughout the reaction, or continuously, such as by means of a pump, through out the reaction. Highly desirably, the aluminum phosphate is added to the reactor or otherwise contacted with the Group 6 metal compound prior to addition of the aluminum hydrocarbyl compound. Intermittent or continuous addition of aluminum hydrocarbyl compound may prolong the catalyst lifetime.

It may be helpful under some operating conditions to pre-activate the catalyst in order to avoid an induction period. In one method, the catalyst is heated to 60-120° C. in the presence of the aluminum phosphate compound prior to addition of the hydrocarbylaluminum compound and olefin. A suitable period for such pretreatment is from, 1 to 10 minutes. In another method, the catalyst and aluminum phosphate mixture is incubated in a solution of the hydrocarbyl aluminum compound, suitably at a temperature from 20 to 50° C., prior to addition of the olefin. In this method a suitable incubation period is from one minute to 20 minutes. According to either method, uptake of olefin occurs rapidly upon contacting with the active catalyst composition.

A diluent or solvent may be used in the process if desired. Preferred diluents or solvents include aliphatic or aromatic hydrocarbons, especially toluene, $C_{5-10}$ alkanes or cycloalkanes or mixtures thereof, and $C_{2-8}$ olefins, especially the olefin or olefin mixture used as the addition monomer or produced by the invention. A most preferred diluent is heptane.

The oligomeric α-olefin product can be recovered and separated by normal means such as fractionation. Alternatively, the oligomeric products can be oxidized and hydrolyzed in situ using known procedures to produce primary alcohols or hydrogenated to produce highly pure alkanes. Polymeric products, if any, are recovered by filtration or devolatilization. Highly desirably, the oligomeric product contains a large quantity of hexene and/or octene. In one embodiment of the invention 1-octene is prepared in high selectivity. That is, the quantity of octene in proportion to total octene and hexene is 30 percent or greater. The productivity of the catalyst compositions is measured in terms of turnovers, or number of ethylene units incorporated into the resulting product. Preferably, turnovers to hexene and octene are at least 300/hr and 150/hr respectively. If a polymeric product is desired, high turnover rates to polymer (greater than 500/hr) are desired as well. Most preferably the polymer incorporates significant quantities of hexene or octene, desirably at least 0.1 units per 1000 carbons total, more desirably at least 0.5 units per 1000 carbons total.

Polymerization, if conducted, is desirably carried out as a continuous polymerization, in which catalyst components, ethylene, and optionally solvent, adjuvants, scavengers, and polymerization aids are continuously supplied to the reaction zone and polymer product continuously removed there from. Within the scope of the terms "continuous" and "continuously" as used in this context are those processes in which there are intermittent additions of reactants and removal of products at small regular or irregular intervals, so that, over time, the overall process is continuous or substantially continuous.

The catalyst compositions can be advantageously employed in a high pressure, solution, slurry, or gas phase polymerization process alone or in combination with any suitable olefin polymerization catalyst. For a solution polymerization process it is desirable to employ homogeneous dispersions of the catalyst components in liquid diluent in which the polymer is soluble under the polymerization conditions employed. One such process utilizing an extremely fine silica or similar dispersing agent to produce such a homogeneous catalyst dispersion where either the metal complex or the cocatalyst is only poorly soluble is disclosed in U.S. Pat. No. 5,783,512. A high pressure process is usually carried out at temperatures from 100° C. to 400° C. and at pressures above 500 bar (50 MPa). A slurry process typically uses an inert hydrocarbon diluent and temperatures of from 0° C. up to a temperature just below the temperature at which the resulting polymer becomes substantially soluble in the inert polymerization medium. Preferred temperatures in a slurry polymerization are from 30° C., preferably from 60° C. tip to 115° C., preferably up to 100° C. Pressures typically range from atmospheric (100 kPa) to 500 psi (3.4 MPa).

Preferably for use in gas phase polymerization processes, the support material and resulting catalyst has a median particle diameter from 20 to 200 μm, more preferably from 30 μm to 150 μm, and most preferably from 50 μm to 100 μm. Preferably for use in slurry polymerization processes, the support has a median particle diameter from 1 μm to 200 μm, more preferably from 5 μm to 100 μm, and most preferably from 10 μm to 80 μm.

The catalyst composition of the present invention can also be employed to advantage in a gas phase polymerization process. Such processes are used commercially on a large scale for the manufacture of polypropylene, ethylene/α-olefin copolymers, and other olefin polymers. The gas phase process employed can be, for example, of the type which employs a mechanically stirred bed or a gas fluidized bed as the polymerization reaction zone. Preferred is the process wherein the polymerization reaction is carried out in a vertical cylindrical polymerization reactor containing a fluidized bed of polymer particles supported or suspended above a perforated plate or fluidization grid, by a flow of fluidization gas.

The gas employed to fluidize the bed comprises the monomer or monomers to be polymerized, and also serves as a heat exchange medium to remove the heat of reaction from the bed. The hot gases emerge from the top of the reactor, normally via a tranquilization zone, also known as a velocity reduction zone, having a wider diameter than the fluidized bed and wherein fine particles entrained in the gas stream have an opportunity to gravitate back into the bed. It can also be advantageous to use a cyclone to remove ultra-fine particles from the hot gas stream. The gas is then normally recycled to the bed by means of a blower or compressor and one or more heat exchangers to strip the gas of the heat of polymerization.

A preferred method of cooling of the bed, in addition to the cooling provided by the cooled recycle gas, is to feed a volatile liquid to the bed to provide an evaporative cooling effect, often referred to as operation in the condensing mode. The volatile liquid employed in this case can be, for example, a volatile inert liquid, for example, a saturated hydrocarbon having 3 to 8, preferably 4 to 6, carbon atoms. In the case that the monomer or comonomer itself is a volatile liquid, or can be condensed to provide such a liquid, this can suitably be fed to the bed to provide an evaporative cooling effect. The volatile liquid evaporates in the hot fluidized bed to form gas which mixes with the fluidizing gas. If the volatile liquid is a monomer or comonomer, it will undergo some polymerization in the bed. The evaporated liquid then emerges from the reactor as part of the hot recycle gas, and enters the compression/heat exchange part of the recycle loop. The recycle gas is cooled in the heat exchanger and, if the temperature to which the gas is cooled is below the dew point, liquid will precipitate from the gas. This liquid is desirably recycled continuously to the fluidized bed. It is possible to recycle the precipitated liquid to the bed as liquid droplets carried in the recycle gas stream. This type of process is described, for example in EP-89691; U.S. Pat. No. 4,543,399; WO-94/25495 and U.S. Pat. No. 5,352,749. A particularly preferred method of recycling the liquid to the bed is to separate the liquid from the recycle gas stream and to reinject this liquid directly into the bed, preferably using a method which generates fine droplets of the liquid within the bed. This type of process is described in WO-94/28032.

The polymerization reaction as well as α-olefin formation occurring in the gas fluidized bed is catalyzed by the continuous or semi-continuous addition of catalyst composition according to the invention. The catalyst composition may be subjected to a prepolymerization step, for example, by polymerizing a small quantity of olefin monomer in a liquid inert diluent, to provide a catalyst composite comprising supported catalyst particles embedded in olefin polymer particles as well.

The polymer is produced directly in the fluidized bed by polymerization of the monomer or mixture of monomers on the fluidized particles of catalyst composition, supported catalyst composition or prepolymerized catalyst composition within the bed. Start-up of the polymerization reaction is achieved using a bed of preformed polymer particles, which are preferably similar to the desired polymer, and conditioning the bed by drying with inert gas or nitrogen prior to introducing the catalyst composition, the monomers and any other gases which it is desired to have in the recycle gas stream, such as a diluent gas, hydrogen chain transfer agent, or an inert condensable gas when operating in gas phase condensing mode. The produced polymer is discharged continuously or semi-continuously from the fluidized bed as desired.

The gas phase processes most suitable for the practice of this invention are continuous processes which provide for the continuous supply of reactants to the reaction zone of the reactor and the removal of products from the reaction zone of the reactor, thereby providing a steady-state environment on the macro scale in the reaction zone of the reactor. Products are readily recovered by exposure to reduced pressure and optionally elevated temperatures (devolatilization) according to known techniques. Typically, the fluidized bed of the gas phase process is operated at temperatures greater than 50° C., preferably from 60° C. to 110° C., more preferably from 70° C. to 110° C.

Uniquely in the present process, α-olefin formation can be induced and optimized in a separate step during the monomer recycle step. That is, a separate reactor and reaction conditions designed for maximum production of the present comonomers, can be inserted into what conventionally is merely a recycle and cooling loop of the gas phase reactor. A separate olefin polymerization catalyst, especially such a catalyst that is optimized for polymer formation or comonomer incorporation, can be used in the usual manner in the gas-phase polymerization reactor to produce polymer products from the olefin mixture produced from the recycled monomer stream. Alternatively, the two catalysts can be used as a mixture, if desired. Thus, according to the invention there is provided a process for preparing copolymers of ethylene and one or more $C_{4-8}$ α-olefins by the direct α-olefin formation and polymerization of ethylene comprising contacting ethylene under oligomer formation conditions with a catalyst composition according to the invention and polymerizing, separately or in the same reactor, at least a portion of the resulting oligomers. Preferably, the process is one in which the ethylene source is recycle of monomer in an ethylene polymerization process.

Suitable gas phase processes which are adaptable for use in the process of this invention are disclosed in U.S. Pat. Nos. 4,588,790; 4,543,399; 5,352,749; 5,436,304; 5,405,922; 5,462,999; 5,461,123; 5,453,471; 5,032,562; 5,028,670; 5,473,028; 5,106,804; 5,556,238; 5,541,270; 5,608,019; and 5,616,661.

EXAMPLES

The skilled artisan will appreciate that the invention disclosed herein may be practiced in the absence of any component which has not been specifically disclosed. The following examples are provided as further illustration of the invention and are not to be construed as limiting. The term "overnight", if used, refers to a time of approximately 16-18 hours, the term "room temperature", refers to a temperature of 20-25° C., and the term "mixed alkanes" refers to a commercially obtained mixture of $C_{6-9}$ aliphatic hydrocarbons available under the trade designation Isopar E®, from Exxon Mobil Chemicals Inc. In the event the name of a compound herein does not conform to the structural representation thereof, the structural representation shall control.

The synthesis of all metal complexes and the preparation of all screening experiments are carried out in a dry nitrogen atmosphere using dry box techniques. All solvents used are HPLC grade and are dried before use.

Chromium (III) tris(bis(trimethylsilyl)amide) is synthesized substantially according to the technique of Bradley et al., *J. Chem. Soc. Dalton*, (1972) 1580-1584. Heptane and nonane are dried by stirring over Na/K alloy and then filtering through dry alumina just before use.

Amorphous aluminum phosphate (AlPO-1) is synthesized substantially according to the technique of Glemza, et al., *ACS Symposium on Catalyst Supports: Chemistry, Formation and Characterization, Div. of Petroleum Chemistry*, New York, Aug. 25-30 (1991). In the process, aluminum nitrate (187.5 g, 0.5 mole) is dissolved in 30 mL water by heating in a beaker to 80° C. Ammonium dihydrogenphosphate (57.7 g 0.5 mole) is then added and the clear solution allowed to cool to room temperature. The solution is transferred to a blender and 67.6 mL of aqueous ammonium hydroxide (1.0 mole) are added during 40 minutes causing an exothermic reaction.

Near the end of the addition, the mixture solidifies. The solid material is transferred to a crystallizing dish and is soaked in a solution of ammonium hydroxide (34 mL, 0.5 mole) and enough water to cover the solids. After soaking overnight the pH of the supernatant is 9.0.

The solids are then extracted in two portions using a Soxhlet™ apparatus and a solution of 30 mL of concentrated ammonium hydroxide in 600 mL of water for 5 hours. The pH of the extracting solution at the end of each extraction is 5.0. The solids are washed with water and then with three portions of acetone before drying in a vacuum oven and then calcining overnight at 600° C. to give 28 g of white solid. Analysis by X-ray diffraction indicated no crystalline order.

Example 1

An automated pressure reactor comprising eight pressure cells with a working liquid volume of each cell of 6 mL is used to prepare ethylene oligomerization and polymerization products. The ethylene is polymer grade and is further purified by passing through an Oxyclear™ purifier (Labclear, Oakland Calif.) and a cylinder of activated molecular sieves (40 nm pore size). Each of the eight glass inserts is charged with 100 mg of AlPO-1 having a particle size between 120 and 230 mesh (125-63 µm) and placed in a 200° C. oven overnight. The tubes are inserted into the pressure cells in the pressure reactor located in a dry box. To each tube is added sequentially 4.9 mL heptane, 0.8 mL of a 0.01 M heptane solution of chromium (III) tris(bis(trimethylsilyl)amide) (8 µmol Cr), and 40 mg nonane (internal standard). These mixtures are heated to 40° C. with stirring for 30 minutes. In all cases, the supernatant is a pale green color indicating incomplete deposition of the Cr compound. To each tube is then added 0.48 mL of a 0.05 M solution of TEAL in heptane (24 µmol, 3 eq.). The reactor head is put in place and each vessel heated to 70° C. before pressurizing with ethylene to the desired pressure. After suitable reaction times, the reactors are vented and the liquid analyzed by GC/MS. Solids are dried and weighed. Ethylene conversions as a function of pressure for hexene, octene and polymer and including a linear best fit (for pressures in psi) are shown in FIG. 1.

Examples 2-5

The reaction conditions of Example 1 are substantially repeated using different hydrocarbyl aluminum activator compounds (trimethylaluminum (TMA), triisobutylaluminum (TiBA), triethylaluminum (TEAL) and triisobutylaluminum modified methylalumoxane (MMAO)) in a 4:1 molar ratio to chromium (III) tris(bis(trimethylsilyl)amide) catalyst. Reactions are conducted at 70° C., 100 psi (700 kPa) ethylene, for 60 minutes. Essentially no 1-butene nor 1-decene are detected in the product mixture. Results are shown in Table 1.

TABLE 1

| Ex. | activator | TO 1-hexene | TO 1-octene | TO PE | Polymer % | octene/ octene + hexene |
|---|---|---|---|---|---|---|
| 2 | TMA | 507 | 227 | 607 | 45 | 0.31 |
| 3 | TiBA | 481 | 235 | 839 | 54 | 0.33 |
| 4 | TEAL | 385 | 186 | 732 | 56 | 0.32 |
| 5 | MMAO | 375 | 163 | 714 | 57 | 0.30 |

[b]turnovers, moles $C_2H_4$/moles Cr

Polymer Composition

Polymer prepared according to Example 4 is analyzed by differential scanning calorimetry (DSC), liquid chromatography (GPC) and $^{13}C$ NMR. $^{13}C$ NMR indicates that 1-hexene is incorporated into the polymer, but no substantial amount of octene is incorporated resulting in an ethylene/hexene copolymer containing 1.6 butyl branches/1000 carbon atoms. Analysis by DSC gives two melting points: 112° C. and 132° C., indicating that two active catalyst sites, incorporating differing amounts of 1-hexene, are likely present. The polymer also has a bimodal molecular weight distribution. Thus, by combining a high octene incorporating catalyst (such as a metallocene, especially the compositions disclosed in U.S. Pat. Nos. 5,703,187, 5,965,756, or 6,015,868) in separate reactors, two copolymer products, one an ethylene/hexene copolymer and the other an ethylene/octene copolymer may be prepared.

Examples 6-17

A number of chromium (III) compounds are tested using AlPO-1 support. Compounds tested are: chromium (IV) tetrakis(t-butoxide), chromium (IV) tetrakis(trimethylsilylmethyl), chromium (III) tris(3,5-heptandionate), chromium (III) tris(2-ethylhexanoate), chromium(II) bis(diphenylamide)(THF)$_2$, chromium (III) trisdi(cyclohexyl)amide, chromium (III) trisdi(isopropyl)amide), chromium (III) trisdi (ethyl)amide, and chromium (III) tris(di(trimethylsilylamide). Results are contained in Table 2a for reactions conducted at 70° C. and 100 psi (700 MPa), 4 equivalent of TiBA activator, heptane solvent and in Table 2b for reactions conducted using 0.35 percent Cr on AlPO-1, at 40° C., 150 psi (1.0 MPa) using 4 equivalents of TEAL activator and heptane solvent.

TABLE 2a

| Ex. | Chromium source | Al/Cr[a] | TO hexene[b] | TO octene[b] | TO PE[b] | PE % | C8/C6 |
|---|---|---|---|---|---|---|---|
| 6 | Cr(IV)(t-butoxide)$_4$ | 4 | 194 | 74 | 6286 | 96 | 0.38 |
| 7 | Cr(IV)(CH$_2$TMS)$_4$ | 4 | 160 | 147 | 6902 | 96 | 0.92 |
| 8 | Cr(III)(3,5-heptandionate)$_3$ | 4 | 175 | 114 | 4518 | 94 | 0.65 |
| 9 | Cr(III)(2-ethylhexanoate)$_3$ | 4 | 67 | 43 | 1643 | 94 | 0.64 |
| 10 | Cr(NPh$_2$)$_2$(THF)$_2$ | 8 | 463 | 0 | 1857 | 80 | 0.0 |
| 11 | Cr(N(TMS)$_2$)$_3$ | 4 | 385 | 186 | 732 | 56 | 0.48 |

[a]Molar Ratio

[b]turnovers, moles $C_2H_4$/moles Cr

TABLE 2b

| Ex. | Chromium source | Hexene % | Octene % | TO hexene[a] | TO octene[a] | TO PE[a] |
|---|---|---|---|---|---|---|
| 12 | $Cr(N(TMS)_2)_3$ | 11 | 9.3 | 1234.6 | 935.1 | 8893.7 |
| 13 | $Cr(III)(N(i-propyl)_2)_3$ | 9.4 | 7.3 | 990.9 | 689.4 | 8693.0 |
| 14 | $Cr(III)(TMP)_3{}^c$ | 12.6 | 8.1 | 990.3 | 570.3 | 6149.4 |
| 15 | $Cr(III)(N(cyclohexyl)_2)_3$ | 4.5 | 4.8 | 113.7 | 108.6 | 2246.1 |
| 16 | $Cr(III)(N(phenyl)_2)_3{}^c$ | 0.9 | 0.7 | 46.6 | 32.4 | 5275.2 |
| 17 | $Cr(N(ethyl)_2)_3$ | 3.3 | 0.4 | 1.2 | 0.1 | 33.9 |

[b]turnovers, moles $C_2H_4$/moles Cr
[c]chromium tris(2,2,6,6-tetramethylpiperidyl amide)

Examples 18-30 Effect of Activator

The reaction conditions of Example 1 are substantially repeated employing several compounds as potential activators, including TMA, TiBA, ethylaluminum dichloride (EtAlCl$_2$), TEAL, tri(isobutyl)alumoxane, available from Akzo Noble, Inc. (IBAO), tri(isobutyl)aluminum modified methylalumoxane, available from Akzo Noble, Inc. (MMAO), diethylaluminum chloride (Et$_2$AlCl), ethylaluminum sesquichloride (Et$_3$Al$_2$Cl$_3$), diethylzinc (Et$_2$Zn), and diethylaluminum ethoxide (Et$_2$AlOEt). Results are contained in Table 3. Runs in which only polymer is produced are labeled as comparative.

TABLE 3

| Ex. | Al reagent | eq./Cr | 1-hexene[b] | 1-octene[b] | PE[b] | % polymer | C8/C6[c] |
|---|---|---|---|---|---|---|---|
| 18 | TMA | 4 | 507 | 227 | 607 | 45 | 0.59 |
| 19 | TiBA | 4 | 481 | 235 | 839 | 54 | 0.65 |
| 20 | EtAlCl$_2$ | 16 | 173 | 0 | 214 | 55 | 0.00 |
| 21 | TEAL | 4 | 385 | 186 | 732 | 56 | 0.64 |
| 22 | IBAO (0.5 hr.) | 4 | 375 | 163 | 714 | 57 | 0.57 |
| 23 | MMAO | 4 | 276 | 158 | 911 | 68 | 0.76 |
| 24 | MMAO | 16 | 639 | 251 | 2741 | 75 | 0.52 |

TABLE 3-continued

| Ex. | Al reagent | eq./Cr | 1-hexene[b] | 1-octene[b] | PE[b] | % polymer | C8/C6[c] |
|---|---|---|---|---|---|---|---|
| 25 | MMAO | 30 | 706 | 166 | 4545 | 84 | 0.31 |
| 26 | MMAO | 100 | 254 | 0 | 1518 | 86 | 0.00 |
| 27 | IBAO (0.5 hr.) | 16 | 298 | 82 | 2589 | 87 | 0.37 |
| 28 | TMA | 16 | 79 | 14 | 973 | 91 | 0.23 |
| 29 | TiBA | 16 | 195 | 0 | 2446 | 93 | — |
| 30 | TEAL | 16 | 106 | 0 | 2902 | 96 | — |

TABLE 3-continued

| Ex. | Al reagent | eq./Cr | 1-hexene[b] | 1-octene[b] | PE[b] | % polymer | C8/C6[c] |
|---|---|---|---|---|---|---|---|
| A* | Et$_2$AlCl | 4 | 0 | 0 | 223 | 100 | — |
| B* | Et$_2$AlCl | 16 | 0 | 0 | 777 | 100 | — |
| C* | Et$_3$Al$_2$Cl$_3$ | 4 | 0 | 0 | 179 | 100 | — |
| D* | Et$_3$Al$_2$Cl$_3$ | 16 | 0 | 0 | 339 | 100 | — |
| E* | Et$_2$Zn | 4 | 0 | 0 | 429 | 100 | — |
| F* | Et$_2$Zn | 16 | 0 | 0 | 304 | 100 | — |
| G* | Et$_2$AlOEt | 4 | 0 | 0 | −143 | 100 | — |
| H* | Et$_2$AlOEt | 16 | 0 | 0 | 152 | 100 | — |

[a]conditions: 70° C., 100 psi (700 kPa), 1 hr. (Ex. 19, 24 = 0.5 hr), AlPO-1, 4 μmol Cr
[b]turnovers, moles $C_2H_4$/moles Cr
[c]weight ratio
*comparative, not an example of the invention Examples 31-38 Effect of Activator/Catalyst Ratio The reaction conditions of Example 1 are substantially repeated with varying ratios of activator (TEAL) to catalyst (chromium (III) tris(di(trimethylsilyl)amide). Results are contained in Table 4. Maximum conversion efficiency, determined as the maximum octene turnover while still obtaining polymer (polyethylene) production at or below 60 percent, preferably at or below 50 percent, is reached at a molar ratio, Al/Cr, of approximately 1/3.

TABLE 4

| Ex. | AlPO-1 mg | μmol Cr | eq. Al | hexene % | octene % | PE % | TO C6[a] | TO C8[a] | TO PE[a] | C8/C6 g/g |
|---|---|---|---|---|---|---|---|---|---|---|
| 31 | 100 | 4 | 1 | 73 | 27 | 0 | 17 | 6 | 0 | 0.37 |
| 32 | 101 | 4 | 2 | 32 | 13 | 55 | 47 | 19 | 80 | 0.41 |
| 33 | 100 | 4 | 3 | 29 | 13 | 58 | 147 | 68 | 295 | 0.47 |
| 34 | 100 | 4 | 4 | 29 | 12 | 59 | 130 | 55 | 268 | 0.42 |
| 35 | 201 | 8 | 1 | 28 | 13 | 59 | 42 | 19 | 89 | 0.46 |
| 36 | 200 | 8 | 2 | 20 | 9 | 71 | 51 | 23 | 179 | 0.45 |
| 37 | 201 | 8 | 3 | 28 | 12 | 60 | 288 | 122 | 607 | 0.42 |
| 38 | 200 | 8 | 4 | 24 | 11 | 65 | 158 | 71 | 420 | 0.45 | conditions: 70° C., 100 psi (700 kPa), 1 hr
[a]turnovers, mol $C_2H_4$/mol Cr.

Examples 39-40 Effect of Support

The reaction conditions of Example 1 are substantially repeated using different support materials, AlPO-1, silica (Sylopol™ 955, available from Grace Davison Inc.), and a phosphated alumina (SMR49-3290, Phosphate on Alumina, available from Grace Davison Inc.). Under varying process conditions AlPO-1 gives hexene and octene in five of the 12 experiments conducted. Phosphated alumina gives hexene and octene in only two experiments and silica makes no hexene or octene under any of the conditions tested. Best results of the experiments are contained in Table 5

TABLE 5

| Ex. support | Hexene % | Octene % | PE % | TO C6[a] | TO C8[a] | TO PE[a] |
|---|---|---|---|---|---|---|
| 39[b] AlPO-1 | 17% | 7% | 76% | 95 | 38 | 413 |
| 40[c] phosphated alumina | 11% | 5% | 84% | 155 | 76 | 1181 |
| I*[d] silica[c] | 0% | 0% | 100% | 0 | 0 | 1315 | conditions: 70° C., 100 psi (700 kPa), 1 hr, 100 mg support
[a]turnovers, mol $C_2H_4$/mol Cr
[b]8 μmol Cr, 24 μmol Al, support dried at 200° C.
[c]8 μmol Cr, 24 μmol Al, support dried at 600° C.
[d]8 μmol Cr, 24 μmol Al, support dried at 600° C.

Example 41 Effect of Aluminum Phosphate Crystallinity

Various crystalline aluminum phosphate molecular sieves are examined to determine the effect of support crystallinity on alkene production. The molecular sieves are further identified in: Flanigen, et al., *J. Am. Chem. Soc.* 1982, 104, 1146-1147, as well as U.S. Pat. Nos. 5,030,431 and 5,552,361, and are synthesized hydrothermally at 100-250° C. from reaction mixtures containing an organic amine or quaternary ammonium salt (R) which becomes entrapped or clathrated within the crystalline products of composition: $xR.Al_2O_3$ (1.0±0.2) $P_2O_5 \cdot yH_2O$, where x and y represent the amounts of nitrogen compound and water needed to fill the microporous voids within the neutral $AlPO_4$ framework. Compared to amorphous aluminum phosphate, the productivity to alkenes using crystalline forms of aluminum phosphate is inferior. Results are contained in Table 6.

TABLE 6

| Ex. support | Hexene % | Octene % | PE % | TO C6[a] | TO C8[a] | TO PE[a] |
|---|---|---|---|---|---|---|
| 41 AlPO-1 | 24% | 10% | 66% | 140 | 61 | 391 |
| 42 AlPO$_4$-14[b] | 22% | 5% | 73% | 73 | 17 | 239 |
| 43 AlPO$_4$-31[b] | 18% | 4% | 77% | 153 | 38 | 650 | conditions: 70° C., 100 psi (700 kPa), 1 hr, 100 mg support, 4 μmol Cr, 4 eq. TEAL
[a]turnovers, mol $C_2H_4$/mol Cr
[b]see, J. Am. Chem. Soc. 1982, 104, at 1147

Examples 44-48 Effect of Al/P Molar Ratio

Various amorphous aluminum phosphate compositions are prepared using differing extraction conditions to control the Al/P ratio of the resulting product. The preparation of ALPO-1 is substantially repeated excepting that prior to Soxlet™ extraction the composition is divided into four portions. One portion (ALPO-2) is not subjected to the final NH$_4$OH Soxhlet™ extraction. A second portion (ALPO-3) is subjected to 2 hours NH$_4$OH Soxhlet extraction (50 mL conc. NH$_4$OH/500 mL water). A third portion (ALPO-4) is subjected to 24 hours NH$_4$OH Soxhlet™ extraction (50 mL conc. NH$_4$OH/500 mL of water). A fourth protion (ALPO-5) is subjected to 24 hours NH$_4$OH Soxhlet™ extraction, but not washed with acetone afterwards. Samples (100 mg) of each support are dried under flowing nitrogen at 200° C. prior to use.

Figure 2:
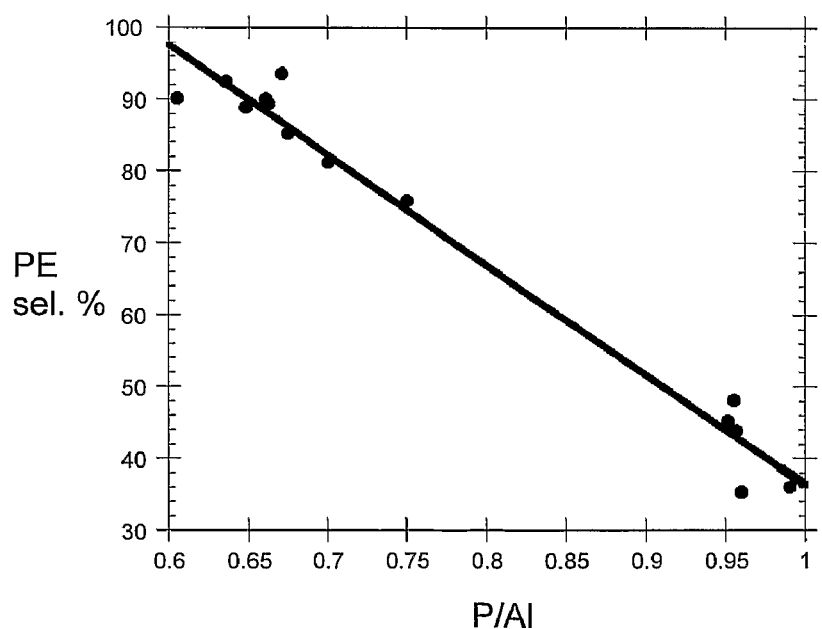
FIG. 2 depicts polymer selectivity as a function of Al/P molar ratio for products prepared in Examples 44-48.

Ethylene is contacted with each supported catalyst in the presence of TIBA and chromium (III) tris(bis(trimethylsilyl) amide). The results are reported in Table 7 and depicted in FIG. 2. The results show that the best selectivity for oligomer formation (poorest selectivity to polymer formation) is obtained at molar ratios P/Al close to 1.0, preferably greater than 0.9, giving a polymer selectivity of less than 50 percent at the conditions tested.

TABLE 7

| Ex. Support | SA[a] (M²/g) | PV[b] (cc/g) | PD[c] (nm) | P/Al | P % | Al % | TO[d] C6 | TO[d] C8 | TO[d] PE | PE sel |
|---|---|---|---|---|---|---|---|---|---|---|
| 44 AlPO-1 | 232 | 1.040 | 18.0 | 0.670 | 22 | 28.6 | 288 | 146 | 6232 | 93% |
| 45 AlPO-2 | 238 | 0.393 | 6.6 | 0.990 | 24.4 | 21.4 | 311 | 139 | 255 | 36% |
| 46 AlPO-3 | 198 | 0.556 | 11.2 | 0.750 | 20.5 | 24 | 153 | 170 | 1014 | 76% |
| 47 AlPO-4 | 252 | 0.84 | 13.3 | 0.700 | 19.8 | 24.7 | 486 | 263 | 3232 | 81% |
| 48 AlPO-5 | 230 | 0.562 | 9.8 | 0.660 | 18.8 | 24.9 | 91 | 85 | 1585 | 90% | conditions: 70° C., 100 psi (700 kPa), 1 hr, 4 μmol Cr(N(TMS)$_2$)$_3$, 16 μmol TiBA.
[a]Surface Area, 5 point BET method
[b]Pore Volume, 5 point BET method
[c]Average Pore Diameter, 5 point BET method
[d]turnovers, mol $C_2H_4$/mol Cr

Examples 49-51 Effect of Support Particle Size

The preparation or ALPO-1 is substantially repeated excepting no extraction with aqueous ammonium hydroxide is conducted. A total of 114 g of material is obtained (93 percent yield). This material is crushed and sieved to obtain 40 g<400 mesh (<38 μm) (ALPO-6), 21 g 200-400 mesh (74-38 μm) (ALPO-7), 24 g 100-200 mesh (150-75 μm) (ALPO-8) and 21 g>100 mesh (>150 μm) (unused). BET and inductively coupled plasma (ICP) spectroscopic analyses indicate that the fractions are compositionally identical.

Samples (100 mg) of the above supports are dried at 200° C. and tested under standard reaction conditions. Smaller particle size supports (AlPO-6) produced greater amounts of polymer. Best selectivity to alkenes is obtained with support particle sizes from 38 to 150 μm, more preferably from 75 to 150 μm. Results are contained in Table 8.

TABLE 8

| Ex. Support | Hexene % | Octene % | PE % | TO C6[a] | TO C8[a] | TO PE[a] |
|---|---|---|---|---|---|---|
| 49 AlPO-6 | 22 | 13 | 65 | 198 | 115 | 588 |
| 50 AlPO-7 | 37 | 16 | 47 | 146 | 63 | 185 |
| 51 AlPO-8 | 46 | 14 | 40 | 126 | 38 | 113 | conditions: 70° C., 100 psi (700 kPa), 1 hr, 4 μmol Cr(N(TMS)$_2$)$_3$, 16 μmol TiBA
[a]turnovers, mole $C_2H_4$/mole Cr

Examples 52-55 Effect of Component Addition Order

The reaction conditions of example 1 are substantially repeated excepting that the order of addition of the various catalyst components to the reactor is changed. Two reactions at each condition are performed. In Example 52, TEAL is added to the reactor after reaching the desired temperature and pressure. In Example 53, TEAL is added last to the composition. In Example 54, chromium (II) tris(bis(trimethylsilyl)amide) is added last. In Examples 55 AlPO-1 is added last. Results, expressed as average turnovers of the two runs are recorded in Table 9. The best procedure is to combine the metal complex and the support and then add the activator (TEAL). Adding the activator after reaching reaction conditions did not result in discernable benefit.

TABLE 9

| Ex. | Last Added Component | TO hexene[a] | TO octene[a] | TO PE[a] |
|---|---|---|---|---|
| 52 | TEAL[b] | 1750 | 1250 | 7100 |
| 53 | TEAL | 1550 | 850 | 4850 |
| 54 | Cr(N(TMS)$_2$)$_3$ | 750 | 650 | 8350 |
| 55 | AlPO-1 | 1150 | 750 | 7600 | conditions: 70° C., 100 psi (700 kPa), 1 hr, 4 μmol Cr(N(TMS)$_2$)$_3$, 16 μmol TiBA
[a]Average Turnovers, mole C$_2$H$_4$/mole Cr
[b]TiBA added after reaching reaction conditions

Examples 56-61 Effect of Reaction Temperature

The reaction conditions of Example 1 are substantially repeated at different reaction temperatures. Results are depicted in Table 10. Best alkene conversion selectivities are obtained at temperatures from 70-85° C. No hexene or octene conversion is noted for this particular combination of support and metal complex at temperatures above 115° C.

TABLE 10

| Ex. | Temp ° C. | TO hexene[a] | TO octene[a] | TO PE[a] |
|---|---|---|---|---|
| 56 | 40 | 65 | 35 | 370 |
| 57 | 55 | 75 | 40 | 260 |
| 58 | 70 | 90 | 45 | 260 |
| 59 | 85 | 75 | 30 | 155 |
| 60 | 100 | 60 | — | 190 |
| 61 | 115 | 30 | — | 120 |
| J* | 130 | — | — | 75 |
| K* | 145 | — | — | 80 | conditions: 100 psi (700 kPa), 1 hr, 4 μmol Cr(N(TMS)$_2$)$_3$, 16 μmol TiBA
*comparative not an example of the invention
[a]turnovers, mole C$_2$H$_4$/mole Cr

Examples 62-69 Effect of Solvent and Ethylene Pressure

The reaction conditions of Example 1 are substantially repeated using heptane or a mixture of heptane and toluene solvents at various ethylene pressures. It may be seen that the presence of the aromatic solvent, toluene, inhibits the rate of hexene and octene formation and mildly increases the rate of polymerization. Results are reported in Table 11.

TABLE 11

| Ex. | C$_2$H$_4$ psi (kPa) | vol % toluene | Hexene % | Octene % | PE % | C6[a] | C8[a] | PE[a] |
|---|---|---|---|---|---|---|---|---|
| 62 | 15 (100) | 0 | 52 | 15 | 33 | 192 | 56 | 121 |
| 63 | 30 (200) | 0 | 43 | 14 | 43 | 313 | 104 | 313 |
| 64 | 50 (350) | 0 | 34 | 14 | 52 | 284 | 119 | 429 |
| 65 | 100 (700) | 0 | 21 | 11 | 67 | 188 | 101 | 594 |
| 66 | 15 (100) | 62 | 25 | 5 | 70 | 89 | 18 | 254 |
| 67 | 30 (200) | 62 | 25 | 7 | 67 | 136 | 40 | 362 |
| 68 | 50 (350) | 62 | 20 | 8 | 72 | 135 | 56 | 478 |
| 69 | 100 (700) | 62 | 12 | 7 | 81 | 102 | 61 | 688 | conditions: 70° C., 1 hr, 4 μmol Cr(N(TMS)$_2$)$_3$, 16 μmol TiBA
[a]turnovers mole C$_2$H$_4$/mole Cr

Examples 70-77 Effect of Electron Donors and Order of Addition

The reaction conditions of Example 1 are substantially repeated with addition of an aprotic polar compound (electron donor) at various times during the reaction. The electron donors tested are tetrahydrofuran (THF) and 1,2-dimethoxyethane (DME). The support is AlPO-9 (100 mg), prepared in the same manner as AlPO-1, excepting that the final extraction is performed using 70 mL of concentrated ammonium hydroxide in 500 mL of water. At the end of the extraction the extracting solution is cloudy and the pH is 6.0 compared to 5.0 for AlPO-1.

When effective, the use of the electron donor generally reduces polymer formation at some loss of octene production. When adding the electron donor before the metal complex, the support, solvent and electron donor are contacted at 40° C. with stirring for 30 minutes followed by addition of the metal complex (Cr). Best results are obtained using limited quantities of electron donor, preferably less than 2 equivalents per mole of metal complex, and adding the electron donor to the support prior to addition of the metal complex. Results are contained in Table 12.

TABLE 12

| Ex. | additive | equivalents | addition order | TO C6[a] | TO C8[a] | C8/C6 g/g | PE % |
|---|---|---|---|---|---|---|---|
| 70 | none | — | — | 545 | 491 | 1.00 | 90 |
| 71 | none | — | — | 411 | 726 | 1.80 | 85 |
| 72 | THF | 2 | before Cr | 845 | 797 | 0.92 | 7 |
| 73 | " | 2 | after Cr | 123 | 69 | 0.55 | 27 |
| 74 | " | 4 | before Cr | 7 | 0 | 0.00 | 97 |
| L* | " | 4 | after Cr | 0 | 0 | — | — |
| 75 | none | — | — | 225 | 173 | 0.75 | 94 |
| 76 | DME | 2 | before Cr | 72 | 59 | 1.14 | 85 |
| M* | " | 2 | after Cr | — | — | — | — |
| 77 | " | 5 | before Cr | 45 | 0 | 0.00 | 0 |
| N* | " | 5 | after Cr | — | — | — | — | conditions: 70° C., 100 psi (700 kPa), 1 hr, 4 μmol Cr(N(TMS)$_2$)$_3$, 16 μmol TiBA
*Comparative, not an example of the invention
[a]turnovers, mol/mol Cr

The invention claimed is:
1. A process for the preparation of oligomeric derivatives of olefin monomers, comprising contacting an olefin monomer or a mixture of olefin monomers under oligomer formation conditions with a catalyst composition to form oligomeric derivatives, wherein the catalyst composition comprises:
   (a) a Group 6 metal amide complex or compound, wherein the Group 6 metal amide complex corresponds to the formula

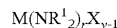

wherein,

M is a Group 6 metal;

R¹ independently in each occurrence is a secondary or tertiary alkyl group of from 3 to 20 carbons, a cycloalkyl group of from 5 to 20 carbons, an aryl or alkylaryl group of from 6 to 20 carbons, or a tri($C_{1-20}$)hydrocarbylsilyl group, and optionally two R1 groups on the same or adjacent amide groups may be joined together thereby forming a heterocycloaliphatic ring, or an alkyl-, aryl-, cycloalkyl-, or trihydrocarbylsilyl- substituted derivative thereof;

X is an anionic ligand of up to 20 atoms not counting hydrogen, and optionally one or more X groups and/or one or more $NR^1_2$ groups may be joined together to form an aliphatic or aromatic ring, r is a number greater than 0 and less than or equal to v; and v is the valence of M, (b) a Group 1, 2, 12, 13 or 14 metal hydrocarbyl composition or compound, and (c) a solid support comprising aluminum phosphate, and wherein the oligomeric derivatives comprises an α-olefin product mixture of greater than 10 percent 1-octene and less than 90 percent 1-hexene, with less than 10 percent of all other α-olefin reaction products, and optionally polymer.

2. The process of claim 1 wherein the olefin monomers is ethylene.

3. A process for the catalytic oligomerization of ethylene to yield an α-olefin product mixture, wherein the α-olefin product mixture comprises greater than 10 percent 1-octene and less than 90 percent 1-hexene, with less than 10 percent of all other α-olefin reaction products, and optionally polymer, comprising a Poisson distribution of 1-hexene and 1-octene products characterized in that the catalyst composition comprises a Group 6 metal amide complex or compound, a Group 1, 2, 12, 13 or 14 metal hydrocarbyl composition or compound, and a solid support comprising aluminum phosphate.

4. A process for preparing a copolymer of ethylene and $C_{4-8}$ α-olefins by oligomerizing ethylene according to claim 1 or 3 to provide an olefin mixture and polymerizing the olefin mixture with ethylene in the presence of the same oligomerizing catalyst composition or a different catalyst composition.

5. A process according to claim 4 in which the ethylene source is recycle of monomer in an ethylene polymerization process.

6. A process according to claim 4 wherein a mixture of catalyst compositions or a second olefin polymerization catalyst is employed.

* * * * *